United States Patent [19]

Merger et al.

[11] Patent Number: 5,068,398

[45] Date of Patent: Nov. 26, 1991

[54] PREPARATION OF 6-AMINOCAPROIC ESTERS

[75] Inventors: Franz Merger, Frankenthal; Rolf Fischer, Heidelberg; Wolfgang Harder, Weinheim; Claus-Ulrich Priester, Ludwigshafen; Uwe Vagt, Speyer, all of Fed. Rep. of Germany

[73] Assignee: BASF Aktiengesellschaft, Ludwigshafen, Fed. Rep. of Germany

[21] Appl. No.: 448,900

[22] Filed: Dec. 12, 1989

[30] Foreign Application Priority Data

Dec. 24, 1988 [DE] Fed. Rep. of Germany ....... 3843792

[51] Int. Cl.$^5$ ............................................ C07C 205/02
[52] U.S. Cl. ..................................... 560/156; 560/155

[58] Field of Search ........................... 548/543; 549/9; 560/156, 155

[56] References Cited

U.S. PATENT DOCUMENTS 2,777,873  1/1957  Haeek .
4,766,237  8/1988  Hutmacher et al. .

Primary Examiner—Werren B. Lone
Assistant Examiner—Margaret Argo
Attorney, Agent, or Firm—Keil & Weinkauf

[57] ABSTRACT

6-Aminocaproic esters are prepared by reacting alkyl 5-formylvalerates with excess ammonia and hydrogen in the presence of ruthenium catalysts at elevated temperature under superatmospheric pressure in liquid ammonia as reaction medium.

11 Claims, No Drawings

PREPARATION OF 6-AMINOCAPROIC ESTERS

According to a process disclosed in U.S. Pat. No. 2,777,873, 6-aminocaproic esters are obtained by reacting 5-formylvaleric esters with ammonia and hydrogen in the presence of hydrogenation catalysts and alkanol solvents at above 100° C. under superatmospheric pressure The yields obtained in this process are still in need of improvement for practice in industry. This process has the further disadvantage that the yield of the aminating hydrogenation, which in the case of isopropyl 5-formylvalerate as starting material is still as high as 70%, decreases dramatically on using the esters of 5-formylvaleric acid with primary alkanols such as ethanol.

An alternative process, described in DE-A-3,602,378, produces 6-aminocaproic esters by reacting 5-formylvaleric esters with ammonia and hydrogen in the presence of hydrogenation catalysts and alkanol solvents at from 40° to 95° C. It is true that this process gives good yields, but the presence of alkanols has a disadvantage that they need to be separated off before the 6-aminocaproic esters are used and an additional, distillation step is undesirable because of the low thermal stability of 6-aminocaproic esters. In addition, the space-time yield of the process still leaves something to be desired for practice in industry.

It is an object of the present invention to provide a process for preparing 6-aminocaproic esters from 5-formylvaleric esters where the space-time yield is high and where, what is more, there is no need to use an alkanol solvent which must be separated off by distillation.

We have found that this object is achieved by a process for preparing a 6-aminocaproic ester by reacting a 5-formylvaleric ester with ammonia in excess and hydrogen in the presence of a hydrogenation catalyst at elevated temperature under superatmospheric pressure by performing the reaction in liquid ammonia as reaction medium and in the presence of a ruthenium catalyst.

The novel process has the advantage that there is no need to use an alkanol and consequently no need to separate off an alkanol. It has the further advantage that its space-time yield is high and by-product formation is low. Yet another advantage of the process is that improved catalyst lives are obtained.

Preferred 5-formylvaleric esters are alkyl 5-formylvalerates, in particular those of $C_1$-$C_4$-alkanols. Suitable starting compounds are for example methyl, ethyl, propyl, isopropyl and n-butyl formylvalerates. Of particular importance in industry is methyl 5-formylvalerate.

The reaction is carried out in liquid ammonia, which functions not only as a reactant but also as solvent. In general, from 1 to 6 kg of ammonia are used per kg of 5-formylvaleric ester. Particularly good results are obtained by using 1.2 to 3.6, in particular from 1.2 to 2.4, kg of ammonia per kg of 5-formylvaleric ester.

The reaction is carried out at elevated temperature. In general, the temperature is from 80° to 140° C., advantageously from 100° to 135° C., in particular from 110° to 130° C.

It is advantageous to use from 1 to 20 moles of hydrogen per mole of 5-formylvaleric ester by carrying out the reaction under superatmospheric pressure, advantageously by maintaining a hydrogen partial pressure of from 40 to 1,000 bar, preferably from 50 to 500 bar, in particular from 70 to 200 bar.

According to the invention, the catalyst used is ruthenium. It is possible to use ruthenium in the form of a finely divided suspension. It is preferable, however, to use ruthenium supported on a carrier. Suitable carriers are for example aluminum oxide, silica gel, titanium dioxide, zirconium dioxide, magnesium aluminates and magnesium silicates. Preferred carriers are aluminum oxide and magnesium aluminates, in particular α-alumina. The ruthenium is applied to the carrier in a conventional manner by impregnating the carrier with an aqueous solution of a ruthenium salt, such as ruthenium chloride or ruthenium nitrate, and subsequent drying with or without calcination. The ruthenium concentration on the carrier is in general from 0.1 to 10% by weight, preferably from 0.5 to 5% by weight, in particular from 1 to 3% by weight. The supported ruthenium catalyst is in general activated in a stream of hydrogen, advantageously at from 180° to 250° C., in particular at from 190° to 230° C., for example within from 1 to 20 hours, preferably from 1.5 to 10 hours.

In general, the weight hourly space velocity over the catalyst is from 0.1 to 15 kg of 5-formylvaleric ester per kg of catalyst per hour. A particularly useful weight hourly space velocity over the catalyst is from 1 to 10, in particular from 4 to 10, kg/kg/h.

The reaction can be carried out batchwise, for example in a high pressure vessel. Preferably, however, the reaction is carried out continuously, for example in a stirred vessel cascade, for example in 2–4 vessels. It has proved advantageous to avoid back mixing during the reaction. It is therefore particularly advantageous to pass a mixture of 5-formylvaleric ester and ammonia together with hydrogen over a fixed bed catalyst in a tubular reaction zone. It is particularly advantageous to use the liquid phase procedure for this purpose. It comprises feeding an essentially upright tubular reaction zone (length:diameter ratio of for example from 8:1 to 50:1), which contains the fixed bed of catalyst, with 5-formylvaleric ester, liquid ammonia and hydrogen from below and withdrawing 6-aminocaproic ester, ammonia and any excess hydrogen at the top of the tubular reaction zone.

In a preferred continuous process, the residence time follows from the catalyst space velocity and the supply of ammonia. It is advantageously within the range from 0.5 to 20 minutes, preferably from 1 to 10, in particular from 2 to 6, minutes.

After excess ammonia has been separated off, for example by distillation or stripping with an inert gas such as $N_2$, the product comprises a 6-aminocaproic ester mixed with the water of reaction.

6-Aminocaproic esters are suitable for preparing caprolactam.

The process according to the present invention is illustrated by the following Examples:

EXAMPLE 1

A vertical tube reactor (diameter, 16 mm, fill level: 15 cm, oil heated jacket) was packed with 10.3 g of catalyst comprising 1.08% of ruthenium on alumina in the form of 1.5 mm extrudates (catalyst preparation: diffusion impregnation of alumina with aqueous ruthenium chloride solution and drying at 70° C. After the temperature had been raised in stages from 100° to 220° C. the catalyst was reduced at 220° C. by passing through it a 10:1 nitrogen/hydrogen mixture at a rate of 50 standard l/h for 80 minutes and hydrogen at a rate of 20 standard l/h for 120 minutes). Thereafter a stream of 78.0 ml (79.9 g, 0.555 mol) of methyl 5-formylvalerate and 280 ml (168 g, 9.9 mol) of liquid ammonia per hour was pumped upward through the reactor at 98 bar and 127° C. together with a stream of hydrogen at a rate of 68 standard 1 (3.0 mol) per hour.

The exit stream was depressurized to atmospheric and passed downward at 40° C. through a 15 cm long column (packed with 5 mm glass rings) through which nitrogen was blown in countercurrent at a rate of 20 l/h. The water-containing exit stream obtained at the base of the column at a rate of 88.2 g per hour contained according to a quantitative analysis by gas chromatography 80.3% of methyl 6-aminocaproate and caprolactam, corresponding to a yield of 88.0% of methyl 6-aminocaproate and 5.8% of caprolactam, based on methyl 5-formylvalerate used.

EXAMPLE 2

A vertical tube reactor (diameter: 9 mm, fill level: 37 cm, oil heated glass jacket) was packed with 14.8 g of the catalyst described in Example 1 (1.08% ruthenium on alumina) which was then activated as described in Example 1.

Thereafter a stream of 120.0 ml (122.9 g, 0.853 mol) of methyl 5-formylvalerate and 374.6 ml (224.8 g, 13.2 mol) of liquid ammonia per hour was pumped upward through the reactor at 98 bar and 129° C. together with a stream of hydrogen at a rate of 65 standard 1 (2.9 mol) per hour.

The exit feed was depressurized to atmospheric and worked up as described in Example 1. The water-containing exit feed obtained at the base of the column at a rate of 135.7 g per hour was found by a quantitative analysis by gas chromatography to contain 81.0% of methyl 6-aminocaproate and 3.3% of caprolactam, corresponding to a yield of 88.9% of methyl 6-aminocaproate and 4.6% of caprolactam, based on methyl 5-formylvalerate used.

EXAMPLE 3

The tube reactor described in Example 2 was packed with 17.2 g (25 ml) of a catalyst comprising 2.78% of ruthenium on alumina, which was prepared as described in Example 1 and activated with hydrogen at a rate of 20 standard l/h by raising the temperature from 100° to 220° C. in the course of 7 hours and then leaving it at 220° C. for 6 hours.

After cooling down to 129° C., a stream of 66 standard 1 (2.9 mol) of hydrogen, 111.0 ml of methyl 5-formylvalerate (purity: 98.4%; 111.8 g, 0.776 mol) and 304.2 ml (182.5 g, 10.7 mol) of liquid ammonia per hour was pumped upward through the reactor at 98 bar.

The exit feed was depressurized to atmospheric via a pressure control valve and passed downward at 20° C. through a 15 cm long column (packed with 5 mm glass rings) through which nitrogen was blown in countercurrent at a rate of 20 l/h. The water-containing exit feed obtained at the base of the column at a rate of 125.5 g per hour was found by quantitative analysis by gas chromatography to contain 77.1% of methyl 6-aminocaproate and 3.0% of caprolactam. The yields based on methyl 5-formylvalerate used were 86.0% of methyl 6-aminocaproate and 4.3% of caprolactam.

EXAMPLE 4

The tube reactor described in Example 2 was packed with 11.0 g of a catalyst comprising 1.08% of ruthenium on alumina in the form of 1.5 mm extrudates, and the catalyst was reduced with hydrogen at a rate of 10 standard l/h over 200 minutes by increasing the temperature in stages from 100° to 200° C.

Thereafter a stream of 52 standard l/h (2.3 mol) of hydrogen, 66.0 ml (67.6 g, 0.469 mol) of methyl 5-formylvalerate and 393.7 ml (236.2 g, 13.9 mol) of liquid ammonia per hour was pumped upward through the reactor at 98 bar and 128° C.

The exit stream was depressurized to atmospheric via a pressure control valve and worked up as described in Example 1. The water-containing exit feed obtained at the base of the column at a rate of 74.6 g per hour was found by quantitative analysis by gas chromatography to contain 79.7% of methyl 6-aminocaproate and 2.6% of caprolactam.

The yields based on methyl 5-formylvalerate were 87.4% of methyl 6-aminocaproate and 3.6% of caprolactam.

EXAMPLE 5

The reactor described in Example 2 was packed with 17.7 g of the catalyst comprising 2.78% of ruthenium on alumina, and the catalyst was activated at 40 bar with a stream of hydrogen at a rate of 20 standard l/h by raising the temperature from 30° to 220° C. in the course of 7 hours and then keeping it at 220° C. for 6 hours.

After cooling down to 128° C., a stream of 53.5 standard 1 (2.4 mol) of hydrogen, 108.0 ml of methyl 5-formylvalerate (purity: 95%; 105.1 g, 0.730 mol) and 240 ml (144 g, 8.5 mol) of liquid ammonia per hour was pumped upward through the reactor at a pressure of 98 bar.

The exit feed was depressurized to atmospheric and passed downward at 40° C. through a 15 cm long column (packed with 5 mm glass rings) through which nitrogen was blown in countercurrent at a rate of 20 l/h. The exit feed obtained at the base of the column at a rate of 122.1 g per hour was found by quantitative analysis by gas chromatography to contain 79.6% of methyl 6-aminocaproate and 2.8% of caprolactam. The yield based on methyl 5-formylvalerate used was 91.8% of methyl 6-aminocaproate and 4.2% of caprolactam.

The Comparative Example which follows illustrates that nickel catalysts give poorer results and that, moreover, the hydrogenation catalyst is damaged (depleted in nickel). This example is not according to the invention:

COMPARATIVE EXAMPLE

A vertical tube reactor (diameter: 16 mm, fill level: 25 cm, oil heated jacket) was packed with 54.0 g of commercial nickel catalyst comprising 55% by weight of nickel oxide in fine division on magnesium silicate (in the form of extrudates 1.5 mm in diameter). The catalyst was reduced over 18 hours with a 1:1 nitrogen/hydrogen mixture at a rate of 30 standard l/h by raising the temperature in stages from 120° to 320° C.

Thereafter a stream of 20.6 ml (21.1 g, 0.146 mol) of methyl 5-formylvalerate and 111.9 ml (67.1 g, 3.9 mol) of liquid ammonia per hour was pumped upward through the reactor at 98 bar and 120° C. together with hydrogen. The reaction mixture was passed through a cooler into a separator where 11.3 l of exhaust gas was separated off per hour. The exit stream was continuously passed at 40° C. downward through a 40 cm long stripper column (packed with 3 mm $V_2A$ stainless steel mesh wire rings) through which nitrogen was blown in countercurrent at a rate of 20 l per hour. The exit stream obtained at the base of the column at a rate of 23.3 g per hour was found by quantitative analysis by gas chromatography to contain 67.9% of methyl 6-aminocaproate and 6.8% of caprolactam, corresponding to a yield of 74.7% of methyl 6-aminocaproate and 9.6% of caprolactam based on methyl 5-formylvalerate used. The nickel content of the exit stream was 295 ppm, corresponding to a loss of 6.9 mg of nickel per hour.

We claim:

1. A process for preparing a 6-aminocaproic ester which comprises:

reacting a $C_1$–$C_4$-alkyl 5-formylvalerate with excess ammonia and hydrogen in the presence of a ruthenium catalyst at a temperature of from 80° to 140° C. under superatmospheric pressure in liquid ammonia as the reaction medium.

2. The process of claim 1, wherein the alkyl 5-formylvalerate is methyl 5-formylvaleric.

3. The process of claim 1, wherein the reaction temperature is from 100° to 135° C.

4. The process of claim 1, wherein a hydrogen partial pressure of from 40 to 1,000 bar is maintained.

5. The process of claim 1, wherein from 1 to 6 kg of liquid ammonia are used per kg of 5-formylvalerate.

6. The process of claim 1, wherein a supported ruthenium catalyst is used.

7. The process of claim 2, wherein a supported catalyst having a ruthenium content of from 0.1 to 10% by weight is used.

8. The process of claim 1, wherein alumina is used as carrier.

9. The process of claim 1, wherein the weight hourly space velocity of the catalyst is from 0.5 to 15 kg of 5-formylvalerate ester per kg of catalyst per hour.

10. The process of claim 1, wherein the alkyl 5-formylvalerate is passed together with liquid ammonia and hydrogen over a fixed bed supported ruthenium catalyst in tubular reaction zone by the liquid phase procedure with essentially no back mixing.

11. The process of claim 1, wherein a residence time of from 1 to 10 minutes is maintained.

* * * * *